United States Patent

Ahlheim et al.

Patent Number: 5,334,710
Date of Patent: Aug. 2, 1994

[54] COMPOUNDS HAVING NON-LINEAR OPTICAL PROPERTIES

[75] Inventors: Markus Ahlheim, Hartheim; Friedrich Lehr, Efringen Kirchen, both of Fed. Rep. of Germany

[73] Assignee: Sandoz Ltd., Basel, Switzerland

[21] Appl. No.: 50,941

[22] Filed: Apr. 21, 1993

Related U.S. Application Data

[63] Continuation of Ser. No. 875,845, Apr. 29, 1992, abandoned.

[30] Foreign Application Priority Data

Apr. 29, 1991 [DE] Fed. Rep. of Germany ....... 4114049

[51] Int. Cl.$^5$ ............................................. C07C 245/08
[52] U.S. Cl. ..................................... 534/852
[58] Field of Search ........................................ 534/852

[56] References Cited

U.S. PATENT DOCUMENTS 5,204,178  4/1993  Licht et al. .

FOREIGN PATENT DOCUMENTS 0205290  9/1989  European Pat. Off. .
WO 90/15087  12/1990  PCT Int'l Appl. .

*Primary Examiner*—James H. Reamer
*Assistant Examiner*—John Peabody
*Attorney, Agent, or Firm*—Robert S. Honor; Richard E. Vila; Andrew N. Parfomak

[57] ABSTRACT

The invention relates to monomeric or polymeric organic compounds having non-linear optical properties, to their production and to their use as electrooptical, photorefractive or holographic devices, especially as modulators, switches, amplifiers, wave guides, sensors to work as sequence transformation especially frequency doubling. These compounds are compounds of Formula I:

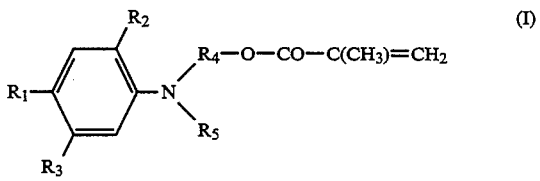

in which $R_1$ is a group for formula a

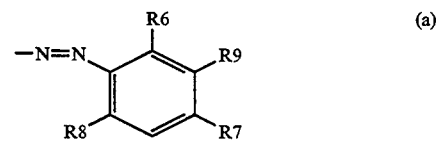

or $R_1$ is a group of formula b

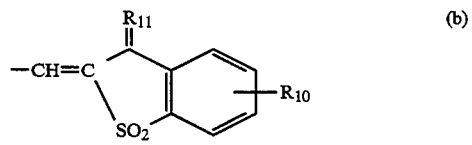

or $R_1$ is an $NO_2$
where $R_1$-$R_{11}$ are organic radicals.

9 Claims, No Drawings

COMPOUNDS HAVING NON-LINEAR OPTICAL PROPERTIES

This is a continuation of application Ser. No. 07/875,845, filed Apr. 29, 1992, now abandoned.

The invention relates to monomeric or polymeric organic compounds having non-linear optical properties, to their production and to their use as optical, integrated optical, electro-optical, photorefractive or holographic devices, especially as modulators, switches, amplifiers, wave guides, sensors and their use for frequency transformation especially frequency doubling. These compounds may also be used as directional couplers.

According to the invention there is provided a compound of formula I:

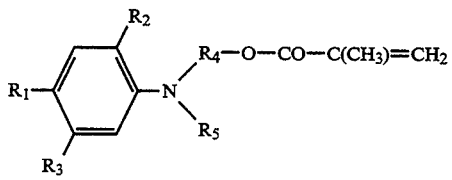

in which $R_1$ is a group for formula a

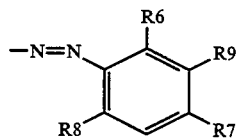

or $R_1$ is a group of formula b

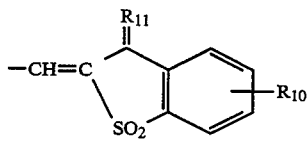

or $R_1$ is $NO_2$ $R_2$, when $R_1$ is a group of formula a), is selected from hydrogen and $C_{1-4}$alkoxy;

$R_2$, when $R_1$ a group of formula b), is hydrogen and $R_2$, when $R_1$ is a nitro group, is selected from hydrogen, halogen, cyano and nitro;

$R_3$, when $R_1$ is a group of formula a) or formula b), is selected from hydrogen, $C_{1-4}$alkyl, $C_{1-4}$alkoxy, and $C_{1-4}$alkylcarbonylamino and $R_3$, when $R_1$ is a nitro group, is hydrogen;

$R_4$ is a $C_{2-6}$alkylene group;

$R_5$, when $R_1$ is a group of formula a) or nitro, is selected from benzyl and phenylethyl, the phenyl group of benzyl or phenylethyl having optionally 1 or 2 substituents selected from $C_{1-4}$alkyl, $C_{1-4}$alkoxy and halogen, and $R_5$, when $R_1$ is a group of formula b) is selected from hydrogen, $C_{1-4}$alkyl, benzyl and phenylethyl, whereby the phenyl group of the benzyl or the phenylethyl group has optionally one or two substituents selected from halogen, $C_{1-4}$alkyl and $C_{1-4}$alkoxy;

$R_6$ is hydrogen, halogen or cyano;

$R_7$ is nitro, cyano or $-C(R_{14})=C(R_{15})(R_{16})$;

$R_8$ is hydrogen, halogen, cyano or nitro;

$R_9$ is hydrogen or when $R_6$ is hydrogen and $R_8$ is nitro, $R_9$ may additionally be SCN;

$R_{10}$ is hydrogen, halogen, $C_{1-4}$alkyl, $C_{1-4}$alkoxy, cyano, nitro, carboxyl or $C_{1-4}$alkoxycarbonyl;

$R_{11}$ is oxygen or a group of the formula $=C(R_{12}R_{13})$, where $R_{12}$ and $R_{13}$ independently are selected from cyano, $C_{1-4}$alkoxycarbonyl, aminocarbonyl and mono and di-$C_{1-4}$alkylaminocarbonyl, $R_{14}$ is hydrogen or cyano; and $R_{15}$ and $R_{16}$ independently are cyano or $C_{1-10}$alkoxycarbonyl.

Further according to the invention there is provided a polymer (homo- or co-polymer) containing recurring units derived from monomer compounds of formula I defined above.

The monomeric compounds according to the invention may therefore also be precursors to form, through polymerization or copolymerization polymeric compounds according to the invention.

Preferably $R_2$ is $R_2'$ where $R_2'$ is hydrogen, or when $R_1$ is $-NO_2$, $R_2$ is additionally nitro.

$R_3$ is preferably $R_3'$ where $R_3'$ is selected from hydrogen, or when $R_2$ is a group of formula a), $R_3'$ may also be methyl.

$R_4$ is preferably $R_4'$ where $R_4'$ is a group of formula $-CH_2CH_2-$ or $-CH_2CH(CH_3)-$ [especially $-CH_2CH_2-$].

$R_5$ is preferably $R_5'$ where $R_5'$, when $R_1$ is a group of formula a) or nitro, is selected from benzyl and phenylethyl (especially benzyl) and $R_5'$, when $R_1$ is a group of formula b), is selected from methyl, benzyl or phenylethyl (especially benzyl or methyl).

$R_6$ is preferably $R_6'$ where $R_6'$ is selected from hydrogen, chloro, bromo or cyano, [especially hydrogen, chloro or cyano].

Preferably $R_7$ is $R_7'$ where $R_7'$ is nitro or dicyano vinyl.

Preferably $R_8$ is hydrogen.

Preferably $R_9$ is hydrogen.

Preferably $R_{10}$ is $R_{10}'$ where $R_{10}'$ is hydrogen or nitro (preferably nitro when $R_{10}$ is in the 5 position).

$R_{11}$ is preferably $R_{11}'$ where $R_{11}'$ is oxygen or a group of the formula $=C(CN)_2$.

The compounds of formula 1 can be produced by esterifiying 1 mol of a compound of formula II

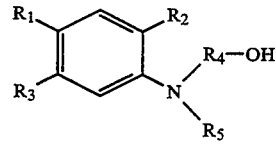

with 1 mol methacrylic acid or a functional derivative of methacrylic acid (preferably the methyl or ethyl ester thereof) or methacryloyl chloride according to known methods.

The compounds of formula I are prepared by the esterification of the OH group attached to $R_4$ in the compounds of formula II with the methacryloyl group.

The compounds of formula II can be made from known compounds by known methods.

The compounds of formula I, in which $R_1$ is a group of formula a) can be prepared by coupling 1 mol of diazotized amine of formula III

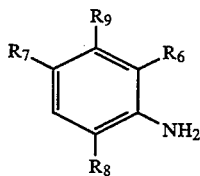

with 1 mol of a compound of formula IV

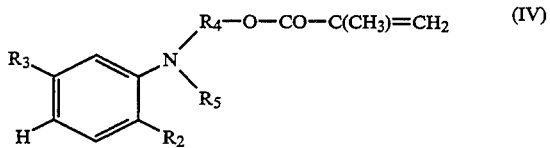

where the symbols are as defined above.

A compound of formula I in which $R_1$ is a group of formula b) can be produced by condensing (by the Knoevenagel reaction) 1 mol of a compound of formula V

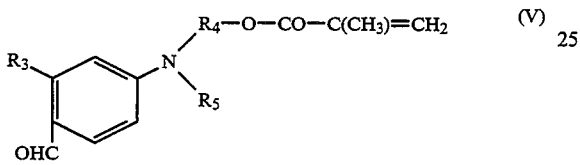

with 1 mol of a compound of formula VI

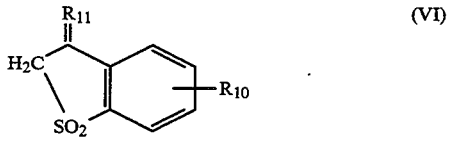

where the symbols are as defined above.

The compound of formulae III to VI are known or may be made from known compounds by known methods.

Polymerizable compounds that can be used to form such copolymers include methacrylic acid $C_{1-4}$alkyl esters, especially methacrylic acid methyl ester.

The monomeric and polymeric compounds according to the invention are generally used in the form of thin films for example for coating of optical or electro-optical pieces to produce a non-linear optical effect, for example in a modulator, an electro optical switch for frequency changing for example frequency doubling. The polymeric films also show very good wave-guiding properties.

The polymers are well soluble in organic solvents so that they can be easily used, for example in a spin coating or dip coating process.

Further, polymers according to the invention have high glass temperatures and a good (i.e. long) stability over time as well as having high non-linear coefficients for electro- optical and non-linear optical effects.

In this specification any $C_{1-4}$alkyl group is preferably $C_{1-2}$alkyl and any $C_{1-4}$alkoxy group is preferably $C_{1-2}$alkoxy.

Under the term halogen is meant chloro, bromo or iodo, especially chloro, bromo, most preferably chloro.

Preferably, the compounds of formula I are water-insoluble or substantially water-insoluble.

More preferably, the compounds of formula I are free or essentially free of water-solubilizing groups.

The invention will now be illustrated by the following examples.

EXAMPLE 1

A. Preparation of N-benzyl-N-βetahydroxyaniline 3000 ml of ethanol and 290 g of sodium acetate are placed in a 10 l sulfonating vessel. While stirring well at room temperature, 411 g. N-(β-hydroxyethyl) aniline and 455.4 g of benzyl chloride are added. This is then warmed to 80° C. and stirred for 6 hours at this temperature. After cooling to room temperature, the mixture is filtered and the filtrate is concentrated in a rotory evaporator and the resulting viscous fluid is allowed to stand in a fridge overnight. The resulting solid is then filtered off.

590 g of N-benzyl N-(β-hydroxyethyl)aniline, the compound of formula 1a

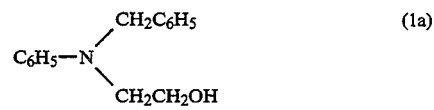

results as a brown oil.

B. Coupling with p-nitroaniline 550 ml of water and 219 g. of a 95% sulfuric acid are stirred drop by drop into a 1.5 l sulfonating vessel. At room temperature, 117.3 g of p-nitroaniline are added and are stirred for about 1 hour. The mixture is then cooled to 0° C. after which 212.5 ml of a 4-N-sodium nitrite solution are added and stirred for a further 3 hours. Finally the excess nitrite is destroyed with sufficient amidosulfonic acid.

193.5 g of N-Benzyl-N-β-hydroxyethylaniline (the compound of formula 1a) in 800 ml of methanol are placed into a 6 l. sulfonating vessel. Over half an hour, the yellow brown diazonium salt suspension is added and with a drop by drop addition of aqueous 30% NaOH solution, the pH is held at 1.5 and the temperature is kept at about 20° C. The mixture is stirred overnight and then the pH is brought up to 4. The mixture is filtered and dried under vacuum at about 60°-80° C.

313 g of a red dyestuff of the formula 1b

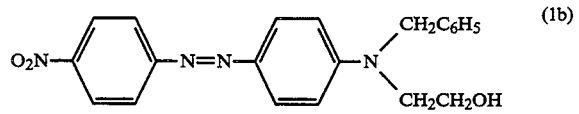

results. After recrystallizing 3 times from toluene, 210 g of the product of formula 1b remain.

C. Reaction with methylacryloyl chloride 1.5 l of dried methylene chloride and 0.6 g hydroquinone are added to a 6 l sulfonating vessel under a nitrogen atmosphere. This mixture is cooled to 0° C. and whilst stirring 83.1 g of methacrylic acid chloride are added. Keeping the mixture at a temperature of between 0°-10° C., a mixture of 1.5 l of dried methylene chloride, 200 g of dyestuff of formula 1b as well as 80.4 g of dried triethylamine are added drop by drop to the mixture.

The reaction mixture is warmed to room temperature slowly and is controlled by the use of thin layers of chromatography (solvent: toluene/acetic acid ester 2:1). After the reaction has finished (3-5 hours) the reaction mixture is filtered and the filtrate is washed 3 times each time with 1 l of 10% aqueous NaOH and finally 3 times, each time with 1 l of water.

The mixture is dried over sodium sulfate and the solvent is removed with a rotory evaporator, whereby 230 g of the red dyestuff of formula 1c

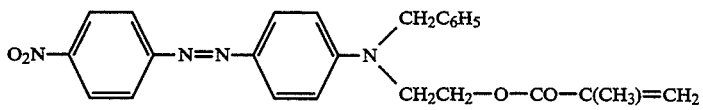

results.

The product can be further purified by dissolving the product 3 times in acetic acid ester and precipitating out again in hexane. 148 g of the dyestuff of formula 1c result (Rf value 0.93, thin layer chromatagraph using Polygram SIL G/UV from Fa. Machery-Nagel in solvent: toluene/ethyl acetate 2:1).

D. Preparation of N-benzyl-N-(β-methacryloxyethyl)-aniline 1000 ml of dried methylene chloride are placed in a 4 l sulfonating vessel at 0° C. together with 334 g of methacrylic acid chloride. A mixture of 500 ml of dried methylene chloride, 323 of dried triethylamine and 454 of N-benzyl-N(β-hydroxyethyl)aniline, (the compound of formula 1a) are added drop by drop to this mixture at 0°-10° C. The reaction mixture is allowed to rise to room temperature slowly and is controlled on a thin layer chromatograph (silica gel) solvent: toluene/acetic acid ester 2:1. After the end of the reaction (after standing overnight), the reaction mixture is filtered and washed three times with one liter of a 10% aqueous NaOH solution and finally four times each time with 1 l of water. The organic phase is then dried over sodium sulphate and the solvent is removed in a rotary evaporator. 482 g of the product of formula 1d

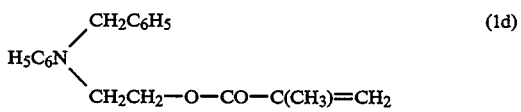

results.

E. Coupling with p-nitroaniline

A mixture of 69 g of p-nitroaniline, 1250 ml of water and 155 ml of 30% hydrochloric acid are stirred together overnight in a 3 liter beaker. After cooling to 0° C., 137 ml of 4-N-sodium nitrite solution is added and allowed to stand under stirring for 3 hours. Finally excess nitrite is destroyed with a little amido sulphonic acid.

A mixture of 800 ml glacial acetic acid, 150 ml of propionic acid and 150 g of the methacrylate of formula 1d above is put into a 4 l sulphonating vessel and cooled to 0° C. The diazonium salt solution is then pumped slowly at 0° C. through a pump whereby the pH is held at 1.5 using sodium acetate. The mixture is stirred overnight and the pH is raised to 4 by the addition of about 300 ml of a 30% aqueous NaOH solution. The mixture filtered and washed with in total 15 l of water. In order to purify the resulting product, the product is suspended 3 times in 2 l of methanol and each time is then filtered. After drying at 40° C. under vacuum, 97 g of the product of formula 1c result. In order to purify the product further, a column chromatograph can be used (silica gel with solvent: chloroform/hexane 1:1).

EXAMPLES 2-8

By a method analogous to that of Example 1 compounds of formula 2

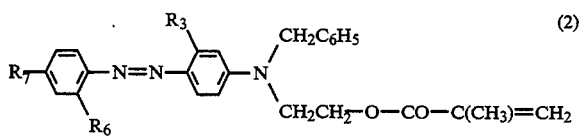

in which $R_3$, $R_6$ and $R_7$ are as given in Table 1 below, can be prepared.

TABLE 1

| Example No. | $R_3$ | $R_6$ | $R_7$ | Rf value |
|---|---|---|---|---|
| 2 | —CH$_3$ | H | —NO$_2$ | 0.92 |
| 3 | H | Cl | —NO$_2$ | 0.93 |
| 4 | —CH$_3$ | Cl | —NO$_2$ | 0.93 |
| 5 | H | —CN | —NO$_2$ | 0.91 |
| 6 | —CH$_2$ | —CN | —NO$_2$ | 0.90 |
| 7 | H | H | —CH=C(CN)$_2$ | 0.74 |
| 8 | —CH$_3$ | H | —CH=C(CN)$_2$ | 0.74 |

Rf values are as measured on thin layer chromatography Polygram SIL G7UV of Fa. Machery-Nagel,
Solvent: Toluene/ethyl acetate 2:1.

EXAMPLE 9

Polymerization of the compound of formula 1c.

0.5 g of the compound of formula 1c (Example 1c) and 9 mg of azobisisobutyronitrile are dissolved in 10 ml of toluene. The mixture is rinsed with oxygen free nitrogen for 3 minutes and then brought into an air tight closed vessel and held therein for 47 hours at 60° C. The remaining solution is then decanted off and the mixture at the bottom of the vessel is then dissolved in 10 ml of tetrahydrofuran. The solution is then filtered and added to 200 ml of methanol and the resultant precipitate polymer is then filtered and dried under vacuum until a constant weight is produced.

EXAMPLES 10-23

By a method analogous to Example 9, polymeric products of the compounds of the formula 9

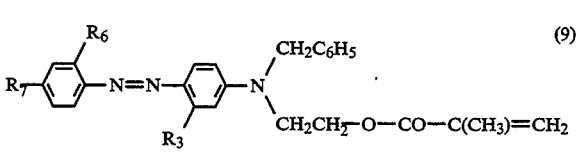

where the symbols $R_3$, $R_6$ and $R_7$ are as in Table 2 below, can be produced from appropriate reactants.

TABLE 2

| Ex. No. | $R_6$ | $R_3$ | $R_7$ | common omer | solvent | ratio Dye/MMA | Tg °C. | λmax nm | solvent |
|---|---|---|---|---|---|---|---|---|---|
| 9 | H | H | $NO_2$ | — | toluene | — | 122 | 454 | $CH_2Cl_2$ |
| 10 | H | $CH_3$ | $NO_2$ | — | S1 | — | 115 | 463 | $CH_2Cl_2$ |
| 11 | Cl | H | $NO_2$ | — | S1 | — | 111 | 476 | $CH_2Cl_2$ |
| 12 | —CN | —$CH_3$ | $NO_2$ | — | S1 | — | 120 | 519 | $CH_2Cl_2$ |
| 13 | Cl | —$CH_3$ | $NO_2$ | — | S2 | — | 111 | 499 | DMF |
| 14 | CN | H | $NO_2$ | — | S2 | — | 115 | 510 | DMF |
| 15 | H | H | $NO_2$ | MMA | S3 | 5/95 | 123 | | |
| 16 | H | H | $NO_2$ | MMA | S3 | 13/17 | 121 | | |
| 17 | H | H | $NO_2$ | MMA | S3 | 26/74 | 120 | | |
| 18 | H | H | $NO_2$ | MMA | S3 | 45/55 | 116 | | |
| 19 | H | H | $NO_2$ | MMA | toluene | 60/40 | 123 | | |
| 20 | H | H | $NO_2$ | MMA | S4 | 66/34 | 109 | | |
| 21 | H | H | $NO_2$ | MMA | toluene | 80/20 | 118 | | |
| 22 | H | H | $NO_2$ | MMA | S4 | 85/15 | 117 | | |
| 23 | Cl | H | $NO_2$ | MMA | toluene | 60/40 | 122 | | |
| 24 | H | H | $CH=C(CN)_2$ | — | S4 | — | | 501 | $CH_2Cl_2$ |
| 25 | H | H | $CH=C(CN)_2$ | — | S4 | — | | 513 | $CH_2Cl_2$ | in which
S1 is toluene:acetone 1/1
S2 is toluene:acetone 2/1
S3 is toluene:acetone 10/1
S4 is toluene:acetone 3/1 and
DMF is dimethyl formamide.

EXAMPLE 26

1.2 ml of phosphoroxychloride are added over 5 minutes to a solution of 2.53 g of N-methyl-N-(β-methacryloyloxyethyl) aniline and 3.2 ml of dimethylformamide in a 50 ml sulphonating vessel. The temperature rises to 60° C. and the reaction mixture is stirred for 5 hours at 70° C. The reaction mixture is then cooled to room temperature and is added dropwise over 5 minutes to a suspension of 2.0 g of 3-cyanomethylene-2,3-dihydro-benzthiophene-1,1-dioxide, 1.97 g of sodium carbonate and 6 ml of methanol. The resulting blue suspension is stirred for 8 hours at room temperature. The reaction mixture is filtered and the residue is washed with 15 ml methanol and 100 ml of water and recrystallised from methanol (Rf value 054 thin layer chromatography as in Example 1c).

EXAMPLES 27-31

Compounds of the formula 27

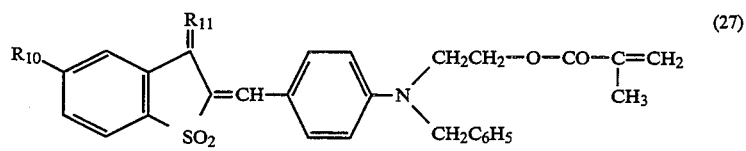

(27)

in which the symbols are as defined in Table 3 can be prepared from appropriate reactants according to the method of Example 26.

$R_f$ values as in Example 1c).

TABLE 3

| Example No. | $R_3$ | $R_{10}$ | $R_{11}$ | Rf values |
|---|---|---|---|---|
| 27 | H | H | $=C(CN)_2$ | |
| 28 | —$CH_3$ | H | $=C(CN)_2$ | 0.70 |
| 29 | H | —$NO_2$ | $=O$ | 0.74 |
| 30 | —$CH_3$ | —$NO_2$ | $=O$ | 0.75 |
| 31 | —$CH_3$ | H | $=O$ | |

EXAMPLE 32-37

By a process analogous to that of Example 9, polymeric compounds derived from monomers of the formula 32

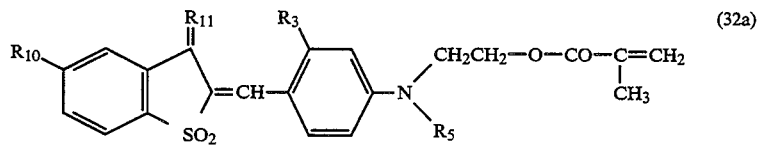

(32a)

in which $R_5$, $R_3$, $R_{10}$ and $R_{11}$ are defined in Table 4 below can be prepared.

TABLE 4

| Ex | $R_5$ | $R_3$ | $R_{10}$ | $R_{11}$ | sol. | Tg [°C.] | λmax nm | solv. |
|---|---|---|---|---|---|---|---|---|
| 32 | —$CH_2C_6H_5$ | $CH_3$ | H | $=C(CN)_2$ | S10 | 156 | 584 | $CH_2Cl_2$ |
| 33 | —$CH_2C_6H_5$ | H | —$NO_2$ | $=O$ | S11 | | 487 | THF |
| 34 | —$CH_2C_6H_5$ | —$CH_3$ | $NO_2$ | $=O$ | S12 | 177 | 500 | DMF |
| 35 | —$CH_2C_6H_5$ | H | H | $=C(CN)_2$ | S13 | 165 | 575 | DMF |
| 36 | —$CH_3$ | H | H | $=C(CN)_2$ | S13 | 136 | 569 | $CH_2Cl_2$ |

TABLE 4-continued

| Ex | R5 | R3 | R10 | R11 | sol. | Tg [°C.] | λmax nm | solv. |
|----|----|----|-----|-----|------|----------|---------|-------|
| 37 | —CH2C6H5 | —CH3 | H | =O | S14 | | | | in which
S10 is DMF:acetone 1/2
S11 is DMF:acetone 3/2
S12 is DMF:acetone 2/3
S13 is toluene:acetone 1/1
S14 is toluene:acetone 2/1
DMF is dimethyl formamide and
THF is tetrahydrofuran.

EXAMPLE 38

To a solution, that has been cooled to −5° C., of 23 g of (N-hydroxyethyl-N-benzyl-2,4-dinitrophenyl)-amine and 30 ml of dry triethylamine in 500 ml of dry methylenechloride, a solution of 7.65 g (7.05 ml) of methacryloylchloride in 30 ml of dried methylene chloride are added drop by drop. At the end of this addition, the mixture is stirred for a further 16 hours at room temperature. The product is then washed (purified) using dilute sodium hydroxide (3 times) and then dried over sodium sulphate and the crude product is then recrystallised from ether after distilling of the solvent.

N-methacryloyloxyethyl-N-benzyl-2,4-dinitrophenyl amine results in good yield.

N-hydroxyethyl-N-benzyl-2,4-dinitrophenyl amine can be produced from N-β-hydroxyethyl-N-benzyl amine and 1,3-dinitro-4-fluoro-benzene by an analogous method.

EXAMPLE 39

Analogous to the method of Example 38, N-methacryloyloxyethyl-N-benzyl-4-nitrophenyl-amine can be produced.

EXAMPLE 40 and 41

By method analogous to that of Example 9, the monomers of Example 37 and 38 can be polymerized. In both examples the solvent is toluene. In Example 40 the Tg is 90 and λ max is 367 nm in CH2Cl2 and in Example 41 the Tg is 107 and λ max is 390 nm in dimethylformamide.

EXAMPLE 42

3 g of the polymer of Example 9 are dissolved over 12 hours at room temperature in mixture of 3.5 ml of tetrahydrofuran and 3.5 ml of N-methylpyrrolidone. In order to remove dust particles, the solution is passed through a filter having an average pore size of 0.2 μm. An indium tin oxide (ITO) covered glass plate from Balzers (26×75 mm) is cleaned as follows: The plate is left overnight in concentrated solution, is washed with distilled water and washed with acetone dried in a vacuum cupboard.

The polymeric solution is spun onto the plates at 800 revs per minute and is finally dried in a vacuum drying cupboard for 12 hours at 100°–110° C. A homogeneous film results having good optical quality. The thickness of the film is 0.83 μm, measured on an Alpha Step (from Fa. Tencor, Rungnis, France).

The film is polarised at 110°–120° C. in a Corona Poling machine at 5K Volt for 30 minutes. The poling process is monitored through SHG measurements according to the "Maker-fringe" methods at 1064 nm (M. A. Mortazari et. al: J. Opt. Soc: Am. B 6 (4) p 733-741 (1989).

At maximum SHG activity, the film is cooled to room temperature while the electric field is still applied. The following SHG are measured:

d 33 (max)=80 pm/V maximum value during poling
d 33 (5d)=54 pm/V SHG value after 5 days at room temperature
d 33 (31d)=52 pm/V SHG value after 31 days at room temperature.

EXAMPLE 43

By a method analogous to that of Example 42, by dissolving the polymer in the appropriate solvent or solvent mixture, and by filtering and spin coating, by poling the polymer film and storing the film at room temperature, the following values are produced.

TABLE 6

| example nc | polymer from Example | d 33 pm/V | d days |
|------------|---------------------|-----------|--------|
| 43 | 10 | 156 | 6 |
| 44 | 11 | 160 | 17 |
| 45 | 12 | 156 | 17 |
| 46 | 15 | 17 | 31 |
| 47 | 16 | 55 | 31 |
| 48 | 17 | 62 | 31 |
| 49 | 18 | 63 | 27 |
| 50 | 20 | 39 | 31 |
| 51 | 22 | 89 | 27 |
| 52 | 34 | 63 | 5 |

What is claimed is:

1. A compound, free of any water soluble groups of formula I

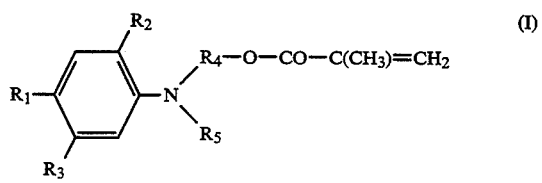

in which R1 is a group of formula a

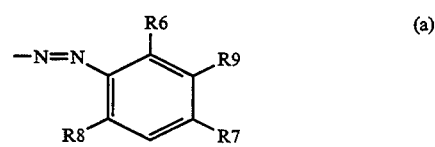

R2, when R1 is a group of formula a), is selected from hydrogen and C1-4alkoxy;
R3, when R1 is a group of formula a) or formula b), is selected from hydrogen, C1-4alkyl, C1-4alkoxyl and C1-4alkylcarbonylamino and
R4 is a C2-6alkylene group;

$R_5$, when $R_1$ is a group of formula a) or nitro, is selected from benzyl and phenylethyl, the phenyl group of benzyl or phenylethyl having optionally 1 or 2 substituents selected from $C_{1-4}$alkyl, $C_{1-4}$alkoxy and halogen, and $R_6$ is hydrogen, halogen or cyano;

$R_7$ is nitro, cyano or $-C(R_{14})=C(R_{15})(R_{16})$;

$R_8$ is hydrogen, halogen, cyano or nitro;

$R_9$ is hydrogen or when $R_6$ is hydrogen and $R_8$ is nitro, $R_9$ is hydrogen or SCN;

$R_{14}$ is hydrogen or cyano; and $R_{15}$ and $R_{16}$ independently are cyano or $C_{1-10}$alkoxycarbonyl.

2. A compound according to claim 1 in which $R_2$ is $R_2'$ where $R_2'$ is hydrogen.

3. A compound according to claim 1 in which $R_3$ is $R_3'$ where $R_3'$ is selected from hydrogen or methyl.

4. A compound according to claim 1 in which $R_4$ is $R_4'$ where $R_4'$ is a group of formula $-CH_2CH_2-$ or $-CH_2-CH(CH_3)-$.

5. A compound according to claim 1 in which $R_5$ is $R_5'$ where $R_5'$, is selected from benzyl and phenylethyl.

6. A compound according to claim 1 in which $R_6$ is $R_6'$ where $R_6'$ is selected from hydrogen, chloro, bromo or cyano.

7. A compound according to claim 1 in which $R_7$ is nitro or dicyano vinyl.

8. A compound according to claim 1 in which $R_8$ is hydrogen.

9. A compound according to claim 1 in which $R_9$ is hydrogen.

* * * * *